United States Patent [19]

Pieringer et al.

[11] Patent Number: 5,444,052
[45] Date of Patent: Aug. 22, 1995

[54] AMPHOTERICIN B COMPOSITION WITH ENHANCED FUNGAL ACTIVITY

[75] Inventors: Ronald A. Pieringer, Lafayette Hill, Pa.; Mary P. Haynes, Largo, Fla.; Haresh S. Ved, Upper Darby; Erlinda A. Cabacungan, Philadelphia, both of Pa.

[73] Assignee: Temple University of the Commonwealth System of Higher Education, Philadelphia, Pa.

[21] Appl. No.: 32,770

[22] Filed: Mar. 16, 1993

Related U.S. Application Data

[63] Continuation of Ser. No. 805,425, Dec. 11, 1991, abandoned.

[51] Int. Cl.$^6$ .............................................. A61K 31/70
[52] U.S. Cl. ...................................... 514/31; 536/6.5; 514/738
[58] Field of Search .................... 514/31, 738; 536/6.5

[56] References Cited

U.S. PATENT DOCUMENTS

| | | | |
|---|---|---|---|
| 4,831,018 | 5/1989 | Kirsh et al. | 514/31 |
| 4,879,274 | 11/1989 | Kamiya et al. | 514/31 |

OTHER PUBLICATIONS

Rudenko, S. V. "Glycerol-Induced Rearrangements . . ." in *Chem. Abstracts* vol. 104, #104375a, 1986.
Takeda Chemical Industries, "Glycerol Derivatives" in *Chemical Abstracts*, vol. 100:121360j, 1984.
Ved et al., *The Journal of Biological Chemistry* 13, pp. 8115-8121, (Jul. 10, 1984).
Ved et al., *The Journal of Biological Chemistry* 13, pp. 8122-8124 (Jul. 10, 1984).
Brissette et al., *The Journal of Biological Chemistry* 14, pp. 6338-6345 (May 15, 1986).
Pieringer et al., *Antibiotic Inhibition of Bacterial Cell Surface Assembly and Function*, pp. 578-581 (1988).
Ved. et al., *Lipids* 2, vol. 25, pp. 119-121 (1990).
Dialog Information Services, File 351: Derwent World Patent Index Acc. No. 76-62629X/33, abstracting Japanese Patent Application 76424/1976 (Jul. 2, 1976).

*Primary Examiner*—Douglas W. Robinson
*Assistant Examiner*—Elli Peselev
*Attorney, Agent, or Firm*—Seidel Gonda Lavorgna & Monaco

[57] ABSTRACT

Fungal infections are treated by administering a combination of
(a) amphotericin B, and
(b) a glycerol ether selected from the group consisting of
 (i) $HOCH_2CHOHCH_2OR$,
 (ii) $HOCH_2CH(OR_1)CH_2OH$, and
 (iii) combinations thereof,
wherein R and $R_1$ are independently selected from the group consisting of $C_8$–$C_{18}$ and $C_8$–$C_{18}$ alkenyl.

The glycerol ether acts synergistically to reduce the minimum inhibitory concentration of amphotericin B. The combination is particularly effective against Cryptococcus and Candida species.

31 Claims, 12 Drawing Sheets

AMPHOTERICIN B COMPOSITION WITH ENHANCED FUNGAL ACTIVITY

This is a continuation of co-pending application Ser. No. 07/805,425 filed on Dec. 11, 1991, now abandoned.

FIELD OF THE INVENTION

The invention relates to antifungal compositions of amphotericin B, and uses thereof.

BACKGROUND OF THE INVENTION

Acquired immune deficiency syndrome (AIDS) is a viral disease for which as yet there is no cure or effective vaccine. Patients with this disease have an immune system that is compromised through the destructive action of virus. This condition leaves the AIDS patient susceptible to opportunistic infections, caused by organisms which rarely cause disease in the healthy individual, but which are responsible for as much as 90% of the mortality of AIDS (Mills et al., *Scientific American*, 263, 50–57 (1986)). Many of these infections are caused by yeasts, which are single cell fungi. Fifty-eight to eighty-one percent of AIDS patients contract fungal infections (Holmberg et al., *Scand. J. Infect. Dis.*, 18, 179–182 (1986)).

*Candida albicans* is the most common cause of fungal infection in AIDS patients. It produces candidal oropharyngitis (thrush), esophagitis, meningitis, and bronchial or pulmonary candidiasis (Id.). The source of the infection is assumed to be endogenous, probably from the intestine.

*Cryptococcus neoformans* is responsible for producing a severe meningitis, which is thought to arise from an initial infection of the lungs. The fungus invades the bloodstream and lodges in the meninges, the membrane covering the brain (Mills et al.,supra). *C. neoformans* spreads more readily than *C. albicans* beyond the skin and mucous membranes. It has a slippery outer coating that impedes macrophages and other immune cells, such as granulocytes, from ingesting the cryptococci (Id.) The coating also helps the fungi resist damage by enzymes from macrophages (Id.).

For the past 30 years, amphotericin B has been the only intravenous antifungal drug available for treating life-threatening fungal infections. It is still the most commonly used antifungal agent. It binds to ergosterol in the fungus' cell membrane. Amphotericin B damages the membrane and causes the internal contents of the fungus to leak out. However, amphotericin B also damages erythrocytes by binding to cholesterol in the cell membrane, causing anemia. Amphotericin B can also harm kidneys.

Because of these toxic effects, amphotericin B cannot be administered in dosages sufficiently high to kill invading fungi. Those patients who survive the disease must receive lifelong preventative therapy of intravenous treatments once or twice a week (Id.).

Fluconazole, an imidazole, has been proposed as an antifungal agent. It must be given orally, and its effectiveness has yet to be established. Fluorocytosine has been used in combination with amphotericin B. It is however, toxic to human cells. Thus, there is a dearth of effective antifungal agents. There is a great need to halt the large number of deaths which occur from opportunistic fungal infections which attack AIDS patients, cancer victims, organ transplant recipients, and other individuals having compromised immune systems.

SUMMARY OF THE INVENTION

A pharmaceutical composition is provided comprising
(a) amphotericin B, and
(b) a glycerol ether selected from the group consisting of
  (i) $HOCH_2CHOHCH_2OR$
  (ii) $HOCH_2CH(OR_1)CH_2OH$, and
  (iii) combinations thereof,
wherein R and $R_1$ are independently selected from the group consisting of $C_8$–$C_{18}$ alkyl and $C_8$–$C_{18}$ alkenyl.

By the term "alkenyl" is meant a mono-, di- or polyunsaturated alkyl group, with monounsaturation, i. e., a single carbon-carbon double bond, being preferred. The glycerol ether is preferably a 1-glycerol ether, that is, a $HOCH_2CHOHCH_2OR$ compound, and/or is preferably a compound wherein R and $R_1$ are selected from $C_{10}$–$C_{14}$ alkyl or alkenyl, more preferably $C_{10}$–$C_{14}$ alkyl, and even more preferably, alkyl.

A method of treating fungal infection is also provided. An effective antifungal amount of amphotericin B and one or more of the above-defined glycerol ethers is administered to a mammal, particularly a human, in need of such treatment.

DETAILED DESCRIPTION OF THE INVENTION

Figure 1:
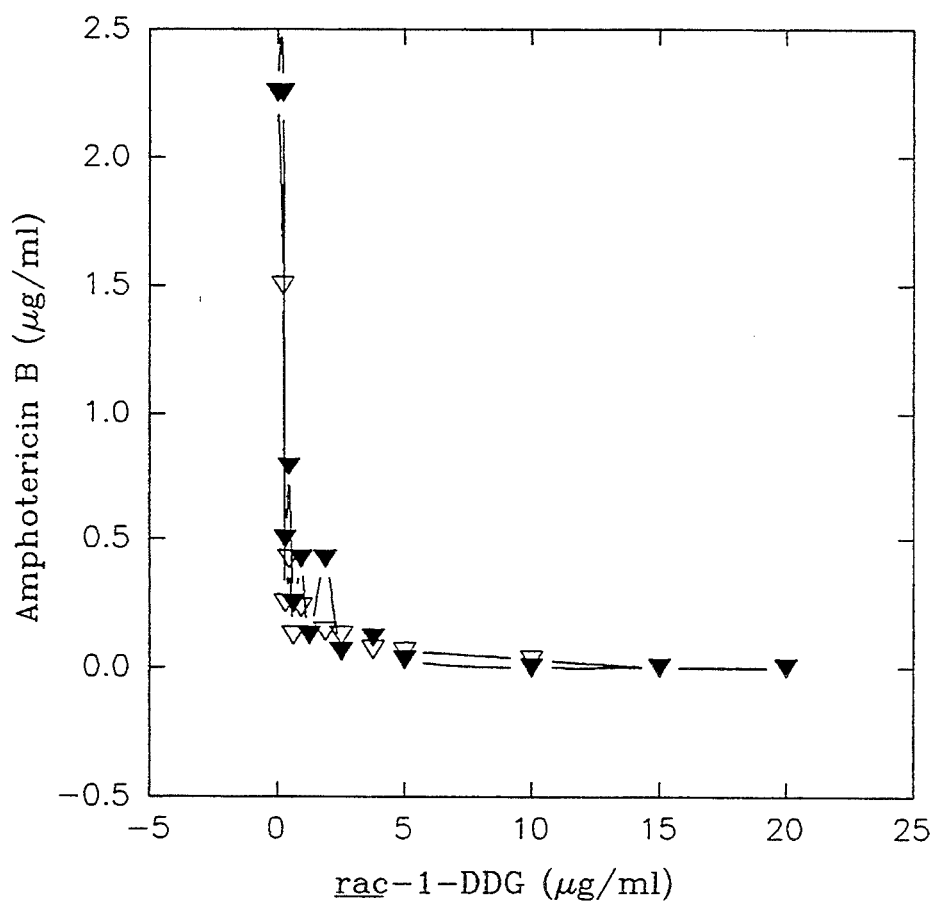
FIG. 1 is a plot of the synergistic antifungal effect of amphotericin B and rac-1-O-dodecylglycerol (rac-1-DDG) against *C. neoformans* in vitro according to a microtiter plate analysis after a 24-hour incubation at 25° C. with the drug combination under continuous shaking and sufficient aeration (▽); and according to an agar plate analysis with the drug combination under the same conditions (▼). Each plot represents an average of three separate trials.

We have found that certain glycerol ethers synergistically potentiate the antifungal activity of amphotericin B, and vice versa. The synergism is significant because amphotericin B alone is too toxic to human cells to be used at intravenous concentrations sufficiently high to completely kill the infecting fungi. The effective antifungal concentration of amphotericin B is lowered through combination with glycerol ether to a concentration which is significantly less toxic to erythrocytes and cells of other host tissues.

Amphotericin B is an antimycotic polyene antibiotic obtained from *Streptomyces nodosus* M4575. Amphotericin B is designated chemically as [1R-(1R*,3S*, 5R*,6R*,9R*, 11R*,15S*,16R*,17R*,18S*,19E,21E,2-3E,25E,27E,29E,31E,33R*, 35S*,36R*,37S,)]-33-[(3-amino-3,6-dideoxy-$\beta$-D-mannopyranosyl)ox-y]1,3,5,6,9,11,17,37-octahydroxy-15,16,18-trimethyl-13-oxo-14,39-dioxabicyclo-[33.3.1]nonatriaconta-19,21,23,25,27,29,31-heptaene-36-carboxylic acid. Crystalline amphotericin B is insoluble in water; therefore, the antibiotic is typically "solubilized" by the addition of sodium desoxycholate to form a mixture which provides a colloidal dispersion for intravenous infusion following reconstitution. While amphotericin B is a potent antifungal agent, it has no effect on bacteria, rickettsiae, and viruses.

Included in the scope of the present invention are all glycerol ethers according to the above formulae, including all optical and geometric isomers satisfying the formulae, and all racemic, diasteriomeric or other mixtures of any such isomers. The 1-glycerol ethers are optically active. According to the 1976 Recommendations for *The Nomenclature of Lipids,* IUPAC-IUB Commission on Biochemical Nomenclature, reported at Lipids 12, 455–468 (1977), carbon atoms of glycerol are numbered stereospecifically. The carbon atom that appears on top in a Fischer projection showing a vertical carbon chain with the C-2 hydroxyl to the left is designated as C-1. To differentiate such numbering from conventional numbering conveying no steric information, the prefix "sn" (for stereospecifically numbered) is used. The prefix "rac" (for racemo) is an equal mixture of both antipodes. According to this convention, the two optical isomers of 1-O-dodecylglycerol are designated as "sn-1-O-dodecylglycerol" and "sn-3-O-dodecylglycerol". The corresponding racemate is designated "rac-1-O-dodecylglycerol".

The glycerol ethers may be synthesized from the appropriate $C_8$-$C_{18}$ saturated or unsaturated alcohol and 1-2-O-isopropylidene glycerol according to the procedure of Bauman et al., J. Org. Chem., 29, 3055–3057 (1964), as also described in Ved et al., *J. Biol. Chem.* 259, 8115–8121 (1984). Briefly, ROH or $R_1$OH, wherein R and $R_1$ are as defined above, is reacted with methanesulfonyl chloride in pyridine. Extraction with ethyl ether and recrystallization from low boiling petroleum ether, e.g. SKELLYSOLVE F (Skelly Oil Co., 1437 Boulder St., Tulsa Okla. 74102) to yield the corresponding alkyl or alkenyl methanesulfonate. This product is reacted with KOH and 1,2-O-isopropylidene glycerol in toluene. After extraction with ethyl ether and hydrolysis by HCl to remove the isopropylidene group, the desired glycerol ether is recrystallized from the petroleum ether. According to this procedure, glycerol ethers of different alkyl or alkenyl chain lengths may be synthesized using the appropriate alcohol as the starting material.

The carbon side chain of the glycerol ether may comprise from a $C_8$ to a $C_{18}$ saturated or mono-, di- or poly-unsaturated branched or unbranched chain. The carbon chain is preferably unbranched and saturated. Carbon chains of from 10 to 14 carbon atoms are particularly preferred.

DDG, a preferred glycerol ether, is a white powder with no odor. Although it is a lipid ether, it has relatively good solubility in water. It melts at 39° C. DDG does not appear to be toxic, even when fed in very high doses to laboratory animals. In a study reported by Weber, *J. Lipid Res.,* 26, 1412–1420 (1985), rac-1-O-dodecylglycerol fed for 4 weeks at a dose of 1 g/kg/day did not significantly alter the organ weights or body weights of mice. Four weeks after removal of the compound from the diet, the lipids of the organs and tissues showed a close resemblance to those of a control group, despite a marked increase in saturated acyl moieties and a concomitant decrease in linoleolyl moieties of total lipids during rac-1-O-dodecylglycerol feeding.

According to the present invention, the glycerol ether and amphotericin B are administered to a mammal, particularly a human being, in amounts sufficient to treat fungal infection. The amount of each drug may vary according to the size, weight, age and sex of the infected individual; whether the treatment is prophylactic or therapeutic; the nature, stage and extent of the infection; the identity of the infecting organism; the route of administration; and other factors. For intravenous administration, the dosage should be adjusted to the requirements of each patient since tolerance to amphotericin B varies. The amount of amphotericin B administered intravenously preferably ranges from about 0.01 to about 1.5 mg per kg of the weight of the individual undergoing treatment, per day. More preferably, the amount is from about 0.025 to about 1.0 mg/kg, most preferably 0.3 to 0.7 mg/kg per day. At an amphotericin B dosage of 1 mg/kg, peak serum concentrations of about 2–3 micrograms/ml are achieved by the end of infusion, and typically remain above 0.5 micrograms/ml for up to 24 hours thereafter. The amount of glycerol ether lipid is any amount which is useful in potentiating the antifungal activity of the amphotericin B. While it is preferred that the two drugs be administered simultaneously, such as in the form of a single pharmaceutical composition, the two agents may also be administered separately, in sequence.

The synergistic interaction between amphotericin B and glycerol ether occurs over a broad range of relative amounts of each substance. The active ingredients may advantageously comprise, on a weight percentage basis, from about 0.4 to about 90 percent amphotericin B and from about 99.6 to about 10 percent glycerol ether, preferably from about 60 to about 40 percent amphotericin B and from about 60 to about 40 percent glycerol ether. The balance of a composition other than the aforementioned active agents comprises a pharmaceutical carrier and optional ingredients.

The composition is administered by any of the routes suitable for administration of amphotericin B. Thus the composition may be primarily administered by topical administration and/or intravenous injection. While it is presently preferred that both active agents are administered through the same route, they may be administered by different routes. For example, it is contemplated that the glycerol ether(s) may be administered orally, and amphotericin B may be administered intravenously. Amphotericin B and the glycerol ether(s) are preferably administered intravenously or topically.

For intravenous administration, the active agents may be administered in combination with any suitable intravenous vehicle containing physiologically compatible substances, such as sodium chloride, glycine, and the like, having a buffered pH compatible with physiologic conditions. Since crystalline amphotericin B is insoluble in water, the vehicle advantageously includes one or more solubilizing agents, most preferably sodium desoxycholate. Amphotericin B for intravenous administration is available as a lyophilized cake providing 50 mg amphotericin B, 41 mg sodium desoxycholate, and 20.2 mg sodium phosphate as a buffer. A colloidal suspension for intravenous infusion is formed upon reconstitution. The glycerol ether component is advantageously dissolved in ethanol and then diluted with sterile water to the effective concentration needed.

Administration of intravenous amphotericin B is advantageously carried out in accordance with existing recommendations for amphotericin B use. Thus, intravenous material should be administered by slow intravenous infusion, preferably over a period of approximately six hours, observing the usual precautions for intravenous therapy.

For topical administration, the active ingredients are contained in any conventional vehicle suitable for topical administration. The topical composition may comprise a cream, ointment or lotion for the treatment of local fungal infection, e.g., cutaneous and mucocutaneous candidal infections. Suitable vehicles used for the topical delivery of amphotericin B are known, and may be advantageously employed in the practice of the present invention. See *Physician's Desk Reference*, 45th Ed., 1991, p. 2147. According to one embodiment, a 3 wt % amphotericin B cream, lotion or ointment is prepared.

The combination of amphotericin B and glycerol ether may be administered to an afflicted mammal to treat fungal infections. More particularly, the combination may be administered to treat any fungal infection previously treated or treatable using amphotericin B alone. Such infections include, but are not limited to, infections by the following fungi: *Histoplasma capsulatum*, *Coccidioides immitis*, various Candida species, *Blastomyces dermatitidis*, Rhodotorula, various Cryptococcus species, *Sporothrix schenckii*, *Mucor mucedo* and *Aspergillus fumigatus*. The foregoing are all inhibited by concentrations of amphotericin B ranging from 0.03 to 1.0 microgram/ml in vitro. The pharmaceutical combination may in particular be used to treat infections of Candida and Cryptococcus, two fungal genii which embrace significant human fungal pathogens, most notably *Candida albicans* and *Cryptococcus neoformans*.

Without wishing to be bound by any theory, it is believed that the glycerol ether enhances the activity of amphotericin B by interfering with fungal capsule synthesis. *C. neoformans* has a polysaccharide capsule which confers virulence to the yeast; acapsular mutants lack virulence in mice (Kozel et al., Rev. Infectious Dis., 10, supplement 2, S436–S439 (1988)). We have observed that *C. neoformans* grown in the presence of glycerol ether produces only small amounts of capsule. What little capsule is synthesized is abnormal in appearance. Without wishing to be bound by any theory, it is believed that elimination of the polysaccharide capsule allows amphotericin B, a lipophilic drug, a greater opportunity to interact with ergosterol in the fungal plasma membrane previously covered by hydrophilic polysaccharides. Inhibition of capsule formation should greatly reduce the virulence of the yeast, and increase the susceptibility of the yeast to phagocytosis. Phagocytes are also stimulated by DDG to ingest foreign substances (Yamamoto et al., *Cancer Immunol. Immunother.*, 25, 185–192 (1987)).

The practice of the invention is illustrated by the following non-limiting examples.

EXAMPLE 1

Determination of rac-1-DDG Minimum Inhibitory Concentration and Synergistic Effect With Amphotericin B on *C. neoformans*

Figure 3:
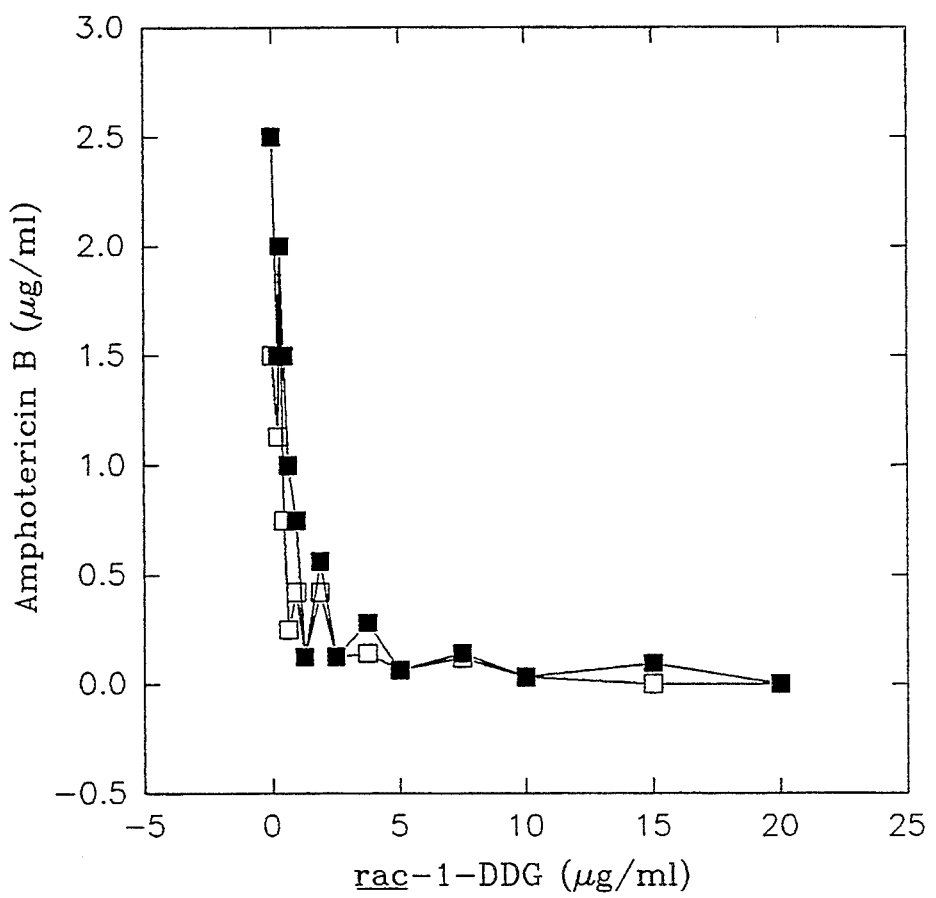
FIG. 3 is similar to FIG. 1, except that the incubation temperature was 37° C. (□, microtiter plate; ■, agar plate).

Lack of growth and viability of *C. neoformans* at graded concentrations of rac-1-O-dodecylglycerol and amphotericin B (Sigma Chemical Co.: 45% amphotericin B, 35% sodium deoxycholate, 20% sodium phosphate), separately and combined, was determined by the "checkerboard" technique of Krogstadt et al., *Fundamentals of Medical Bacteriology and Mycology* (2nd Ed.) 521–525, 544–550 (1980). Briefly, the growth of the fungi was measured in 96 well microtiter plates. A growth medium (100 μl per well) containing graded combinations of DDG and amphotericin B was inoculated with 5 μl of log phase culture of 0.1 optical density at a wavelength of 675 nm. The growth inoculum was measured turbidimetrically. Growth or no growth of each microtiter plate well was determined visually after 24 hours of continual shaking and aeration (microtiter plate analysis). To ensure single cell death, each well visually exhibiting no apparent growth was plated on 2% agar, 1% bactopeptone, 2% glucose plates, incubated at 37° C. for 24 hours and analyzed for growth (agar plate analysis). The data are set forth in FIG. 1 (25° C. incubation followed by microtiter plate analysis (△) and agar plate analysis (▼)) and FIG. 3 (37° C. incubation followed by microtiter analysis (□) and agar plate analysis (■)). Each graph represents an average of three separate trials. The steep hyperbolic curves generated from these data are indicative of strong synergism between amphotericin B and DDG against *C. neoformans*. Synergy is defined as no growth of fungi in the presence of the two antifungal agents, each of which is present at a concentration less than one-half of its MIC. As seen in Table 1, at 25° C. and one-half the MIC for rac-1-DDG (7.5 microgram/ml) the MIC for amphotericin B dropped to 0.047 micrograms/ml from 2.25 micrograms/ml. This represents a 48-fold decrease in the amphotericin B MIC. With amphotericin B present at one-half of its MIC (1.12 micrograms/ml) the rac-1-DDG MIC dropped to 0.125 micrograms/ml, a 120-fold decrease. Viability studies (data not shown) showed that the yeast was killed and not just growth-inhibited by DDG and amphotericin B.

TABLE 1

Cryptococcus Neoformans

| T° C. | Plate Type | Compound | MIC (μg/ml) | ½ MIC (μg/ml) | Added Compound | Resulting MIC (μg/ml) | Fold MIC Decrease |
|---|---|---|---|---|---|---|---|
| 25 | M[1] | rac-1-DDG | 15 | 7.5 | Amph. B | 0.047 | 48 |
| 25 | M | Amph. B | 2.25 | 1.13 | rac-1-DDG | 0.125 | 120 |
| 25 | A[2] | rac-1-DDG | 10 | 5 | Amph. B | 0.0313 | 72 |
| 25 | A | Amph. B | 2.25 | 1.13 | rac-1-DDG | 0.125 | 80 |
| 37 | M | rac-1-DDG | 15 | 7.5 | Amph. B | 0.118 | 12.7 |
| 37 | M | Amph. B | 1.5 | 0.75 | rac-1-DDG | 0.3 | 50 |
| 37 | A | rac-1-DDG | 20 | 10 | Amph. B | 0.0313 | 80 |
| 37 | A | Amph. B | 2.5 | 1.25 | rac-1-DDG | 0.125 | 160 |

[1] Microtiter
[2] Agar

EXAMPLE 2

Figure 2:
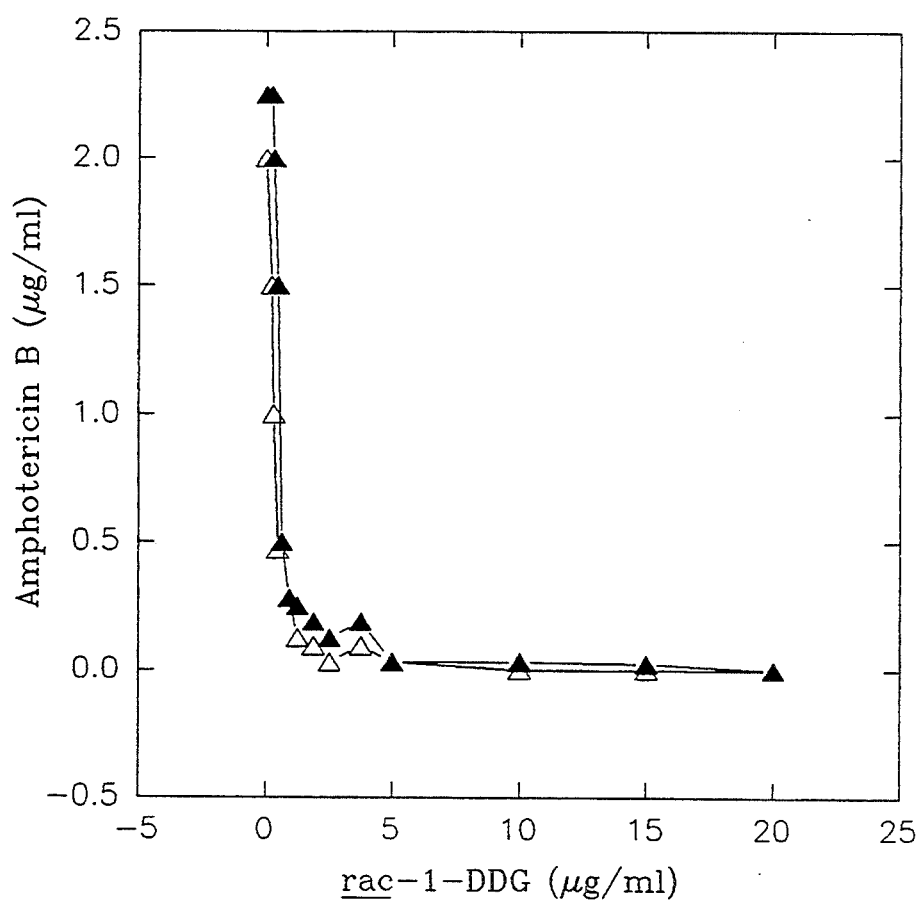
FIG. 2 is a plot of the synergistic antifungal effect of amphotericin B and rac-1-DDG against *C. albicans* under the same conditions of FIG. 1 (△, microtiter plate; ▲, agar plate).
Figure 4:
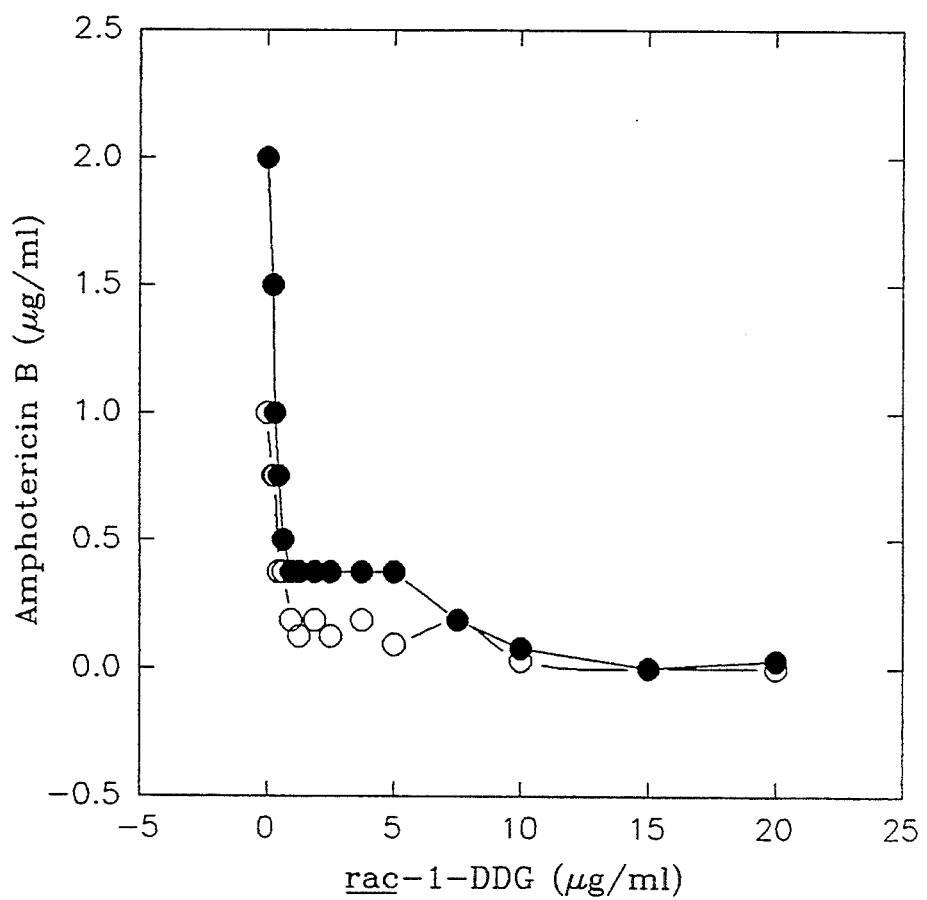
FIG. 4 is similar to FIG. 2, except that the incubation temperature was 37° C. (○, microtiter plate; ●, agar plate).
Figure 5:
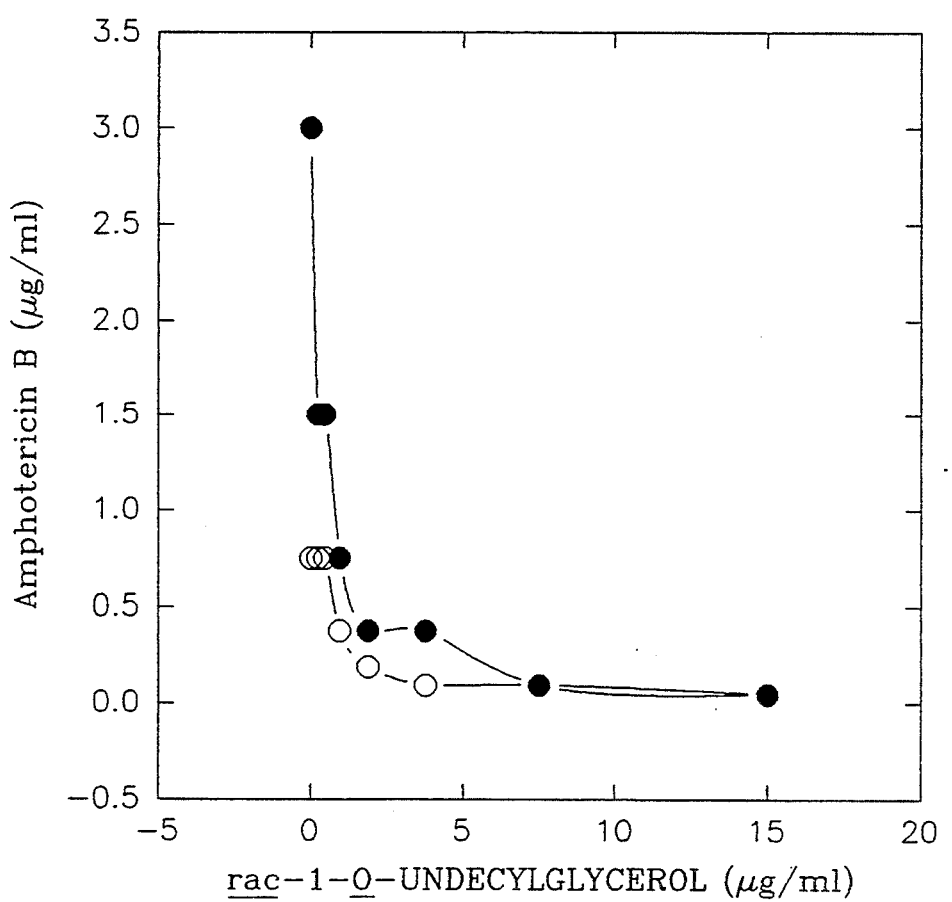
FIG. 5 is a plot of the synergistic antifungal effect of amphotericin B and rac-1-O-undecylglycerol against *C. neoformans* in vitro after 24-hour incubation at 25° C., as determined by microplate analysis (○) and agar plate analysis (●).
Figure 6:
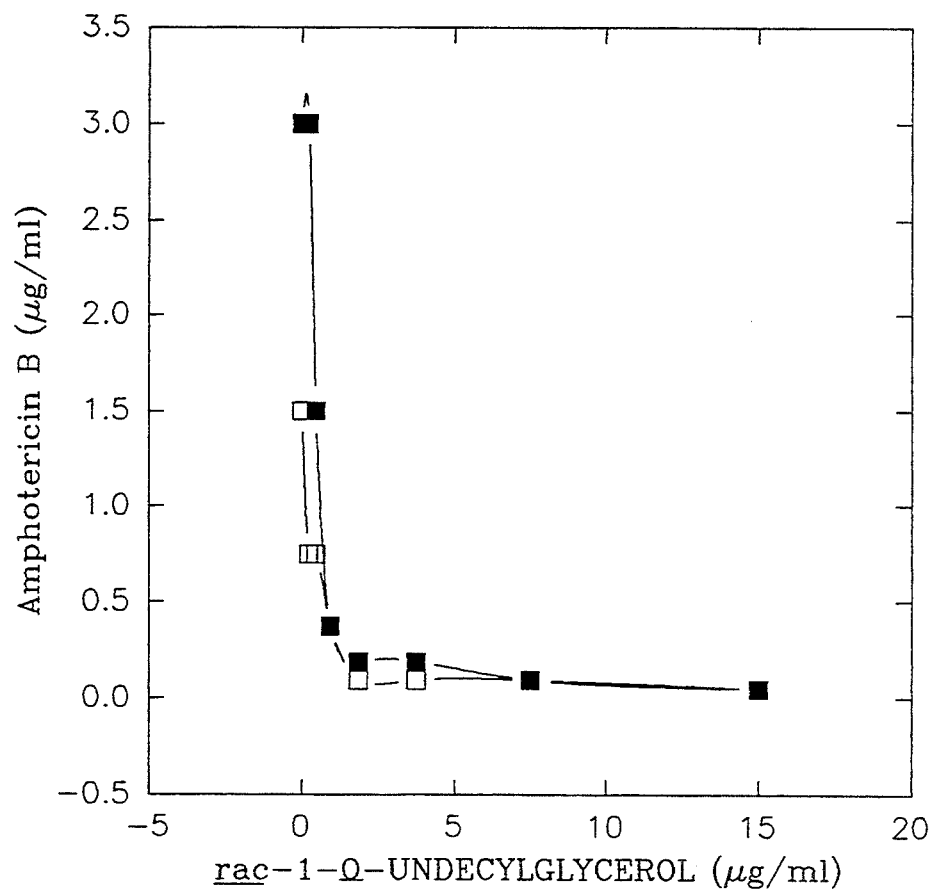
FIG. 6 is similar to FIG. 5, except that the test organism was *C. albicans*. Microplate (□), agar plate (■).
Figure 7:
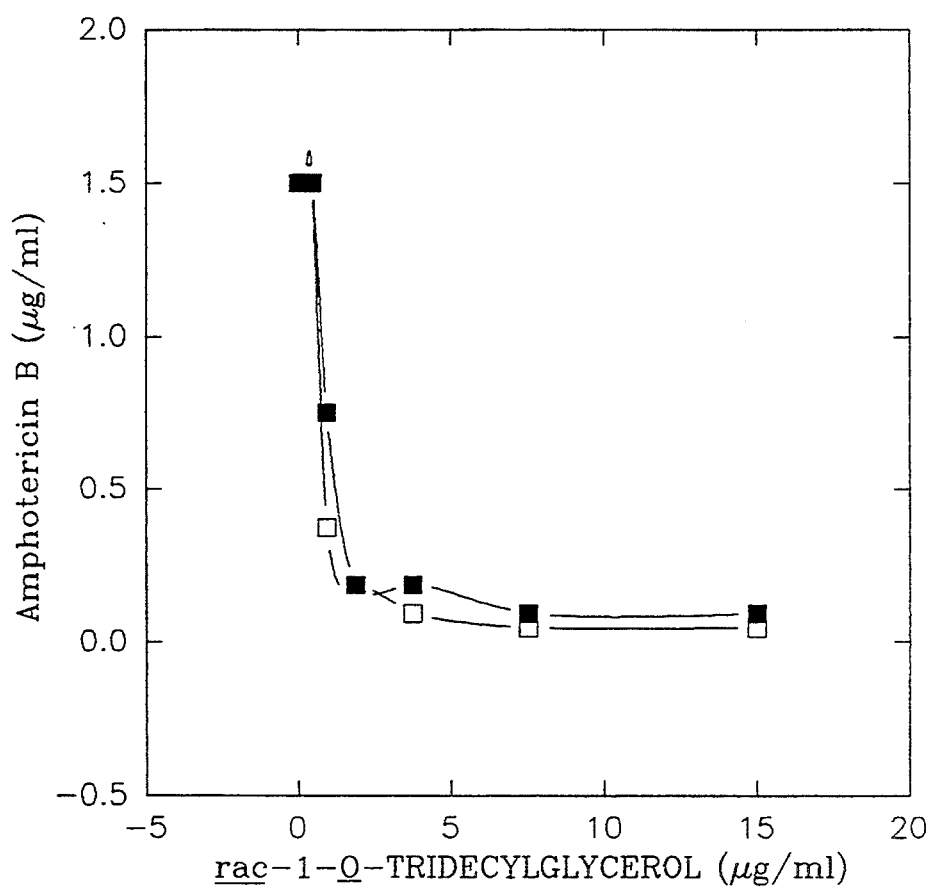
FIG. 7 (*C. neoformans*) is similar to FIG. 5, except that the glycerol ether was rac-1-O-tridecylglycerol. Microplate (□); agar plate (■).
Figure 8:
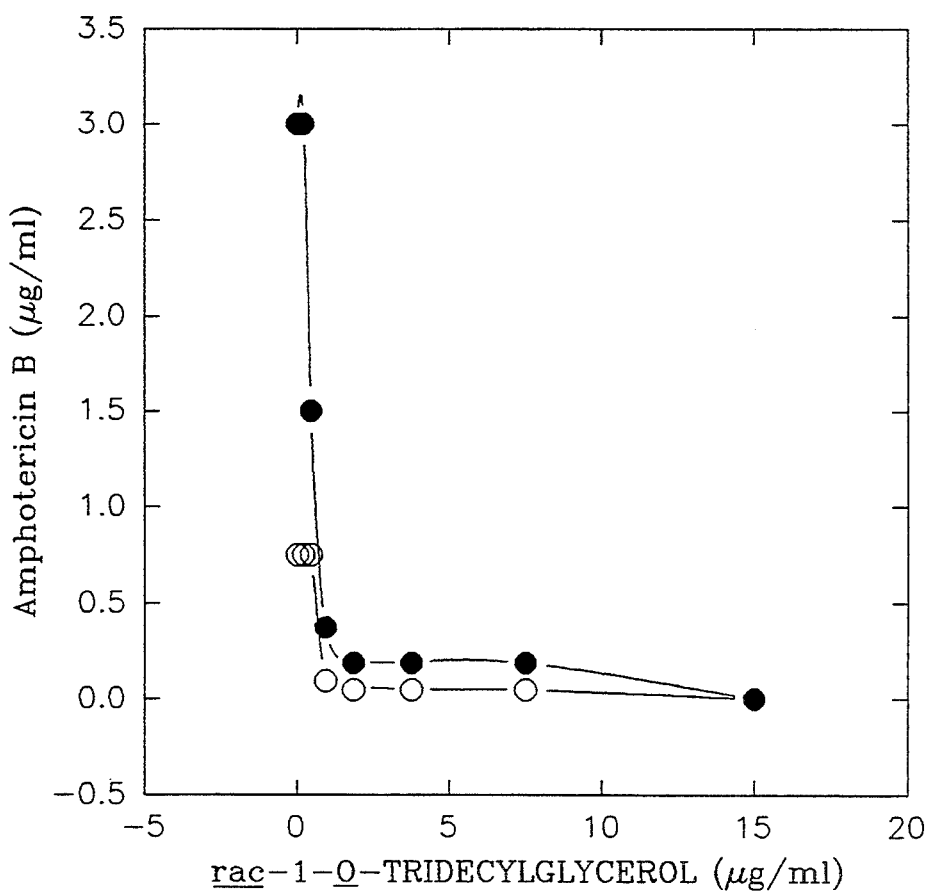
FIG. 8 is similar to FIG. 7, except that the test organism was *C. albicans*. Microplate (○); agar plate (●).
Figure 9:
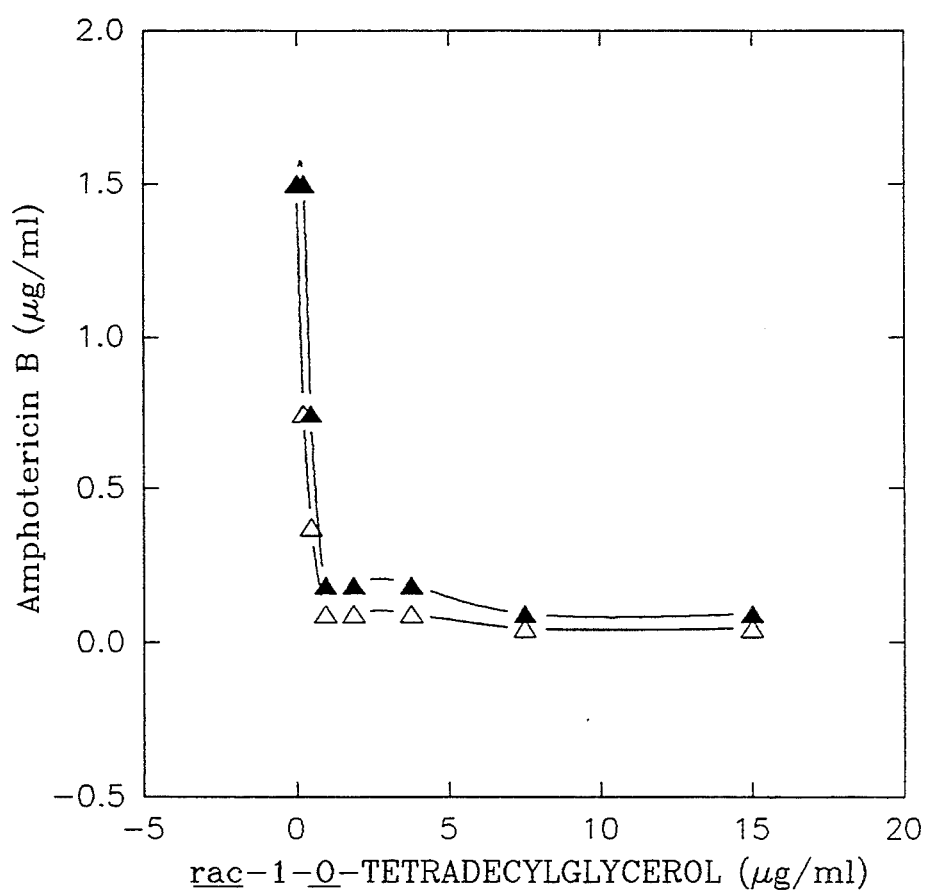
FIG. 9 (*C. neoformans*) is similar to FIG. 5, except that the glycerol ether was rac-1-O-tetradecyl glycerol. Microplate (△); agar plate (▲).
Figure 10:
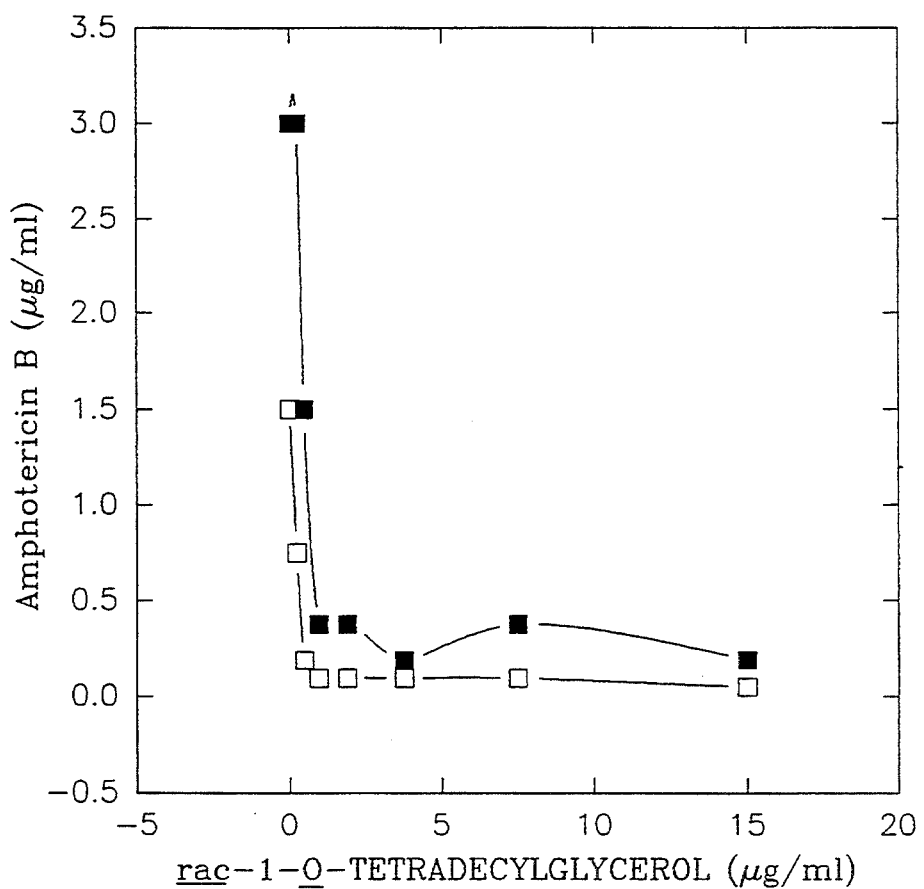
FIG. 10 is similar to FIG. 9, except that the test organism was *C. albicans*. Microplate (□); agar plate (■).

Determination of rac-1-DDG Inhibitory Concentration and Synergistic Effect With Amphotericin B on Candida albicans The procedure of Example 1 was followed, substituting C. albicans for C. neoformans. The data are set forth in FIG. 2 (25° C. incubation followed by microtiter plate analysis (Δ) and agar plate analysis (▲)) and FIG. 4 (37° C. incubation followed by microtiter analysis (○) and agar plate analysis (●)). Each graph represents an average of three separate trials. The steep hyperbolic curves generated from these data are again indicative of strong synergism between amphotericin B and rac-1-DDG. The data are summarized in Table 2.

TABLE 2

Candida Albicans

| T° C. | Plate Type | Compound | MIC (μg/ml) | ½ MIC (μg/ml) | Added Compound | Resulting MIC (μg/ml) | Fold MIC Decrease |
|---|---|---|---|---|---|---|---|
| 25 | M | rac-1-DDG | 10 | 5 | Amph. B | 0.0313 | 64 |
| 25 | M | Amph. B | 2 | 1 | rac-1-DDG | 0.281 | 36 |
| 25 | A | rac-1-DDG | 20 | 10 | Amph. B | 0.0313 | 72 |
| 25 | A | Amph. B | 2.25 | 1.13 | rac-1-DDG | 0.25 | 80 |
| 37 | M | rac-1-DDG | 15 | 7.5 | Amph. B | 0.1875 | 5.3 |
| 37 | M | Amph. B | 1 | 0.5 | rac-1-DDG | 0.375 | 40 |
| 37 | A | rac-1-DDG | 15 | 7.5 | Amph. B | 0.1875 | 10.6 |
| 37 | A | Amph. B | 2 | 1 | rac-1-DDG | 0.375 | 40 |

EXAMPLES 3-8

Determination Of Inhibitory Concentration Of Other Glycerol Ethers And Synergistic Effect With Amphotericin B On C. neoformans And C. albicans The procedure of Examples 1 and 2 was followed utilizing a 24 hour incubation at 25° C. and substituting the following glycerol ethers for rac-1-DDG: rac-1-O-undecylglycerol, rac-1-O-tridecylglycerol and rac-1-O-tetradecylgylcerol. The data are set forth in FIGS. 5-10. Table 3 comprises a key to interpreting FIGS. 5-10.

TABLE 3

| Example | Glycerol Ether | Plate Anaylsis Type | Test Organism | FIG. |
|---|---|---|---|---|
| 3 | rac-1-O-undecylglycerol | M[1]:○; A[2]:● | C. neoformans | 5 |
| 4 | " | M:□; A:■ | C. albicans | 6 |
| 5 | rac-1-O-tridecylglycerol | M:□; A:■ | C. neoformans | 7 |
| 6 | rac-1-O-tridecylglycerol | M:○; A:● | C. albicans | 8 |
| 7 | rac-1-O-tetradecylglycerol | M:△; A:▲ | C. neoformans | 9 |

TABLE 3-continued

| Example | Glycerol Ether | Plate Anaylsis Type | Test Organism | FIG. |
|---|---|---|---|---|
| 8 | rac-1-O-tetradecylglycerol | M:□; A:■ | C. albicans | 10 |

[1] Microtiter
[2] Agar

Each graph represents an average of three separate trials. The steep hyperbolic curves are again indicative of strong synergism between amphotericin B and the glycerol ether.

EXAMPLES 9-14

Figure 11:
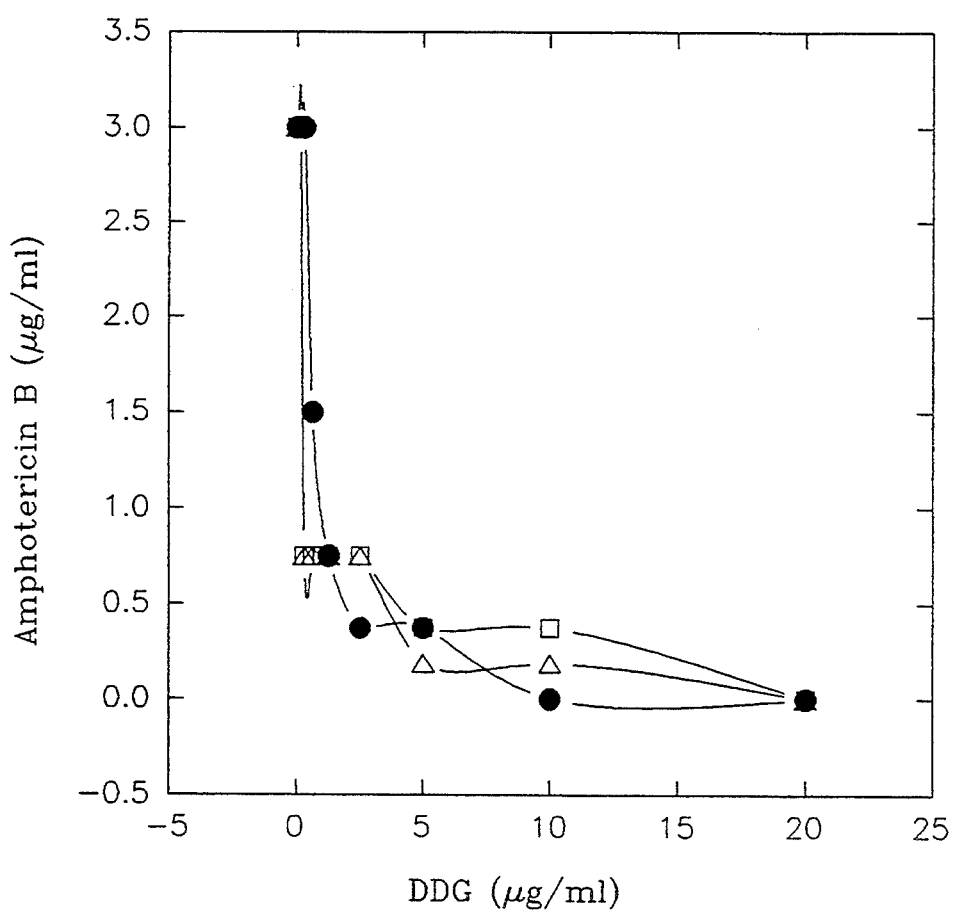
FIG. 11 is a plot of the synergistic effect of 1-DDG (-□-), 2-DDG (-●-) and Sn-3-DDG (-△-) on the antifungal effect of amphotericin B on *C. neoformans* after 24-hour incubation at 37° C.
Figure 12:
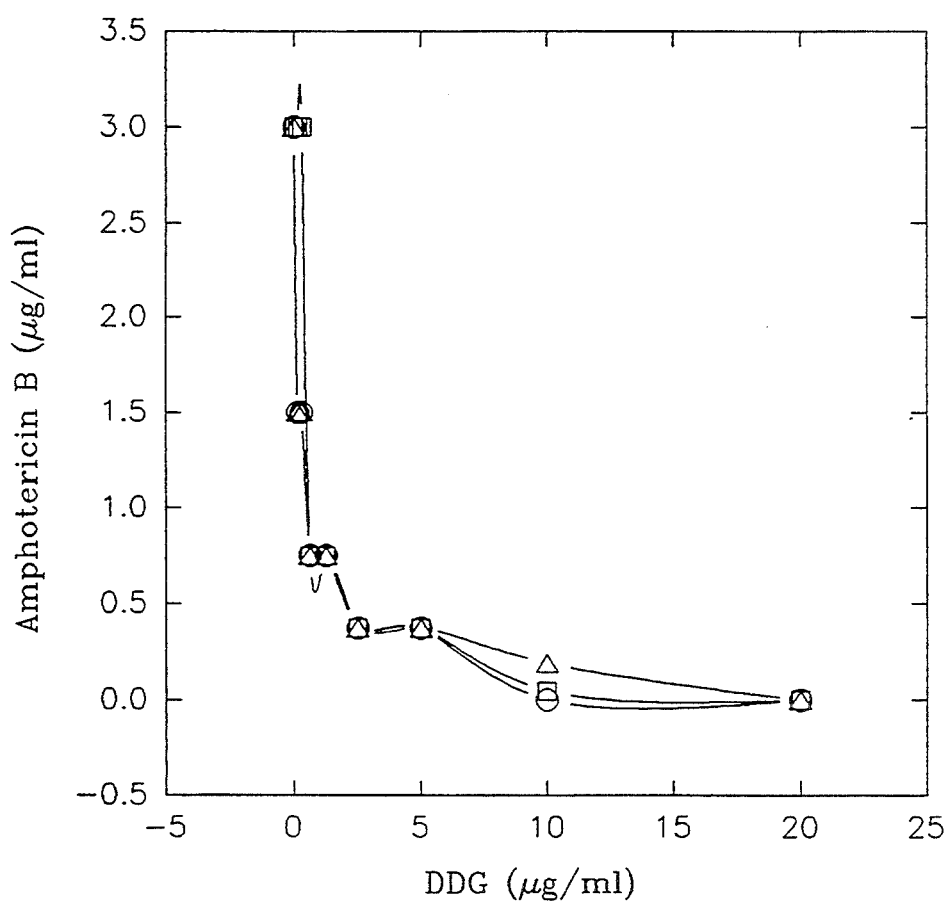
FIG. 12 is similar to FIG. 11, except that the test organism was *C. albicans:* sn-1-DDG (-○-), 2-DDG (-△-) and sn-3-DDG (-□-).

Comparison of Synergistic Effect of DDG Isomers on Amphotericin B Antifungal Activity The procedure of Examples 1 and 2 was followed utilizing a 24 hour incubation time at 37° C., but utilizing DDG isomers in combination with amphotericin B. The data are set forth in FIGS. 11 (Cryptococcus neoformans) and 12 (Candida albicans). Table 4 comprises a key to interpreting FIGS. 11-12.

TABLE 4

| Example | Glycol Ether | Test Organism | FIG. |
|---|---|---|---|
| 9 | sn-1-O-dodecylglycerol | C. neoformans | 11(-□-) |
| 10 | 2-O-dodecylglycerol | C. neoformans | 11(-●-) |
| 11 | sn-3-O-dodecylglycerol | C. neoformans | 11(-△-) |
| 12 | sn-1-O-dodecylglycerol | C. albicans | 12(-○-) |
| 13 | 2-O-dodecylglycerol | C. albicans | 12(-△-) |
| 14 | sn-3-O-dodecylglycerol | C. albicans | 12(-□-) |

The steep hyperbolic curves are indicative of strong synergism between amphotericin B and the glycerol ether. The substantial overlap of curves in FIGS. 11 and 12 indicates that the two 1-DDG optical isomers are substantially equivalent in potentiating the antifungal activity of amphotericin B, and that the 1-DDG optical isomers are substantially equivalent in this respect to the 2-DDG position isomer.

Because *C. neoformans* and *C. albicans* can infect the brain of immunocompromised patients, we carried out studies in which the yeast is added to a primary culture of neurons which are then treated with synergistic concentrations of amphotericin B and rac-1-DDG. Phase contrast microscopy revealed that the concentrations of DDG and amphotericin B which killed the yeasts did not adversely change the growth pattern of the neurons. In fact, DDG is known to actually promote neuronal growth (Ved et al., *J. Neuroscience Res.* 30, 353–358 (1991)).

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A pharmaceutical composition suitable for intravenous administration consisting essentially of
   (a) amphotericin B,
   (b) a glycerol ether selected from the group consisting of
      (i) $HOCH_2CHOHCH_2OR$,
      (ii) $HOCH_2CH(OR_1)CH_2OH$, and
      (ii) combinations thereof,
   wherein R and $R_1$ are independently selected from the group consisting of $C_8$–$C_{18}$ alkyl and $C_{10}$–$C_{18}$ alkenyl, and
   (c) a pharmaceutically acceptable carrier suitable for intravenous administration, wherein the composition consists essentially of, exclusive of the pharmaceutically acceptable carrier, from about 0.4 to about 90 wt. % amphotericin B and from about 10 to about 99.6 wt. % of the glycerol ether.

2. A composition according to claim 1 wherein R an $R_1$ are selected from $C_8$–$C_{18}$ alkyl groups and $C_{10}$-alkenyl groups having one double bond.

3. A composition according to claim 2 wherein the alkyl of alkenyl groups are unbranched.

4. A composition according to claim 3 wherein the glycerol ether is $HOCH_2CHOHCH_2OR$, and R is selected from the group consisting of $C_8$–$C_{18}$ alkyl and $C_{10}$–$C_{18}$ alkenyl groups having one double bond.

5. A composition according to claim 3 wherein R and $R_1$ are alkyl groups independently selected from the group consisting of decyl, undecyl, dodecyl, tridecyl and tetradecyl.

6. A composition according to claim 4 wherein R is an alkyl group selected from the group consisting of decyl, undecyl, dodecyl, tridecyl and tetradecyl.

7. A composition according to claim 5 where R and $R_1$ are dodecyl.

8. A composition according to claim 6 wherein R is dodecyl.

9. A composition according to claim 8 wherein the glycerol ether is sn-1-O-dodecylglycerol.

10. A composition according to claim 8 wherein the glycerol ether is sn-3-O-dodecylglycerol.

11. A composition according to claim 7 wherein the glycerol ether is 2-O-dodecylglycerol.

12. A composition according to claim 1 wherein the composition consists essentially of, exclusive of the carrier, from about 40 to about 60 wt. % amphotericin B and from about 60 to about 40 wt. % glycerol ether.

13. A composition according to claim 12 wherein R and $R_1$ are alkyl groups independently selected from the group consisting of decyl, undecyl, dodecyl, tridecyl and tetradecyl.

14. A composition according to claim 13 wherein R and $R_1$ are dodecyl.

15. A composition according to claim 14 wherein the glycerol ether is sn-1-O-dodecylglycerol.

16. A composition according to claim 14 wherein the glycerol ether is sn-3-O-dodecylglycerol.

17. A composition according to claim 14 wherein the glycerol ether is 2-O-dodecylglycerol.

18. A method of treating fungal infection by a species of the genus Candida or by a species of the genus Cryptococcus comprising intravenously administering to a mammal in need of such treatment an antifungal effective amount of
   (a) from about 0.4 to about 90 wt. % amphotericin B, and
   (b) from about 10 to about 99.6 wt. % of a glycerol ether selected from the group consisting of
      (i) $HOCH_2CHOHCH_2OR$,
      (ii) $HOCH_2CH(OR_1)CH_2OH$, and
      (ii) combinations thereof,
   wherein R and $R_1$ are independently selected from the group consisting of $C_8$–$C_{18}$ alkyl and $C_{10}$–$C_{18}$ alkenyl.

19. A method according to claim 18 wherein R and $R_1$ are selected from $C_8$–$C_{18}$ alkyl groups and $C_{10}$–$C_{18}$ alkenyl groups having one double bond.

20. A method according to claim 19 wherein the alkyl or alkenyl groups are unbranched.

21. A method according to claim 20 wherein the glycerol ether is $HOCH_2CHOHCH_2OR$, and R is selected from the group consisting of $C_8$–$C_{18}$ alkyl and $C_{10}$–$C_{18}$ alkenyl groups having one double bond.

22. A method according to claim 20 wherein R and $R_1$ are alkyl groups independently selected from the group consisting of decyl, undecyl, dodecyl, tridecyl and tetradecyl.

23. A method according to claim 21 wherein R is an alkyl group selected from the group consisting of decyl, undecyl, dodecyl, tridecyl and tetradecyl.

24. A method according to claim 22 wherein R and $R_1$ are dodecyl.

25. A method according to claim 18 comprising administering from about 40 to about 60 wt. % amphotericin B and from about 60 to about 40 wt. % glycerol ether.

26. A method according to claim 25 wherein R and $R_1$ are alkyl groups selected from the group consisting of decyl, undecyl, dodecyl, tridecyl and tetradecyl.

27. A method according to claim 26 wherein R and $R_1$ are dodecyl.

28. A method according to claim 18 wherein the dosage of amphotericin B is from about 0.01 to about 1.5 mg per kilogram of the treated mammal, per day.

29. A method according to claim 28 wherein the dosage of amphotericin B is from about 0.025 to about 1 mg per kilogram of treated mammal, per day.

30. A method according to claim 18 wherein the infecting fungus is *Cryptococcus neoformans*.

31. A method according to claim 18 wherein the infecting fungus is *Candida albicans*.

* * * * *